United States Patent [19]

Haefele

[11] 3,937,807

[45] Feb. 10, 1976

[54] ORAL COMPOSITIONS FOR PLAQUE, CARIES, AND CALCULUS RETARDATION WITH REDUCED STAINING TENDENCIES

[75] Inventor: John William Haefele, Sarasota, Fla.

[73] Assignee: The Procter & Gamble Company, Cincinnati, Ohio

[22] Filed: July 9, 1974

[21] Appl. No.: 486,800

Related U.S. Application Data

[63] Continuation-in-part of Ser. No. 338,463, March 6, 1973, abandoned.

[52] U.S. Cl. ..................... 424/52; 424/49; 424/54
[51] Int. Cl.²... A61K 7/16; A61K 7/18; A61K 7/22
[58] Field of Search ................................. 424/49–58

[56] References Cited
UNITED STATES PATENTS 3,733,399   5/1973   Becker et al........................... 424/54

FOREIGN PATENTS OR APPLICATIONS 490,384   8/1938   United Kingdom................... 424/54

*Primary Examiner*—Shep K. Rose
*Attorney, Agent, or Firm*—Ronald L. Hemingway; Robert B. Aylor; Richard C. Witte

[57] ABSTRACT

Oral compositions such as toothpastes, mouthwashes and the like containing a particular substantive bis-biguanide compound which inhibits the formation of plaque and caries, and a specific amino carboxylate compound which inhibits the tendency of the bis-biguanide compound to produce a stain on oral surfaces, preferably while maintaining the bis-biguanide as a water-soluble salt.

11 Claims, No Drawings

ORAL COMPOSITIONS FOR PLAQUE, CARIES, AND CALCULUS RETARDATION WITH REDUCED STAINING TENDENCIES

CROSS-REFERENCE TO RELATED APPLICATION

This application is a continuation-in-part of my copending application, Ser. No. 338,463, filed Mar. 6, 1973 and now abandoned.

BACKGROUND OF THE INVENTION

The field of this invention is "oral compositions" which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes and topical solutions.

The bis-biguanide compounds of this invention are known, having been disclosed in U.S. Pat. 2,684,924, Rose et al., patented July 27, 1954; U.S. Pat. 2,990,425, Senior et al., patented June 27, 1961; U.S. Pat. 2,830,006, Burtwell et al., patented Apr. 8, 1958; and U.S. Pat. 2,863,019, Burtwell et al., patented Dec. 9, 1958. All of said patents are incorporated herein by reference. The anti-plaque activity of the bis-biguanides is known.

SUMMARY OF THE INVENTION

It has now been discovered that if the specific bis-biguanide compounds disclosed herein and the specific amino carboxylate compounds disclosed herein are used together in the oral cavity in the concentrations set forth herein, with the amino carboxylate compound in a molar excess as set forth hereinafter, and the compounds either being used together or sequentially, the stain that is normally caused by continuous use of the bis-biguanide compounds alone is effectively reduced. It is preferred that the amino carboxylate compound and the bis-biguanide compound be used together.

DETAILED DESCRIPTION OF THE INVENTION

The bis-biguanide compounds of this invention have the generic formula solution compositions. Suitable water soluble salts include the acetate, the hydrochloride, and especially the gluconate salt of the above compounds. Water-insoluble salts are disclosed in my copending applications, Ser. Nos. 338,464 filed Mar. 6, 1973 and 463,495, filed Apr. 24, 1974, said applications being continuations-in-part of application Ser. No. 267,816, filed June 30, 1972, all of said applications being incorporated herein by reference. Water-insoluble salts for the purpose of this application are those having a solubility in 25°C. water of less than about 0.04%. Specific examples of these bis-biguanide compounds are disclosed hereinafter.

The above compounds are effective anti-plaque agents which demonstrate anti-caries activity. However, when compositions containing these compounds are used continuously in a program of oral hygiene, a rather offensive brown stain forms on the oral surfaces which is resistant to removal by ordinary brushing with conventional dentifrices. This stain problem prevents compositions containing these bis-biguanide compounds from being accepted by the consumer. The bis-biguanide compounds are normally used in amounts of from about 0.01 to about 2.5% by weight of the composition, preferably from about 0.05% to about 1.2%, and most preferably from about 0.1% to about 0.8%. Depending upon the composition, lesser or greater amounts may be used. In general, all that is required is to have an effective amount of the bis-biguanide salt in the mouth sufficient to give anti-plaque and/or anti-caries effectiveness.

The specific amino carboxylate compounds which have been found to be effective in preventing stain, but which do not precipitate the bis-biguanide compound are nitrilo triacetic acid (NTA) and hendic and (2-hydroxyethylnitrilodiacetic acid), and the water-soluble salts of these amino carboxylates. The pharmaceutically acceptable water-soluble salts, e.g., sodium, potassium, ammonium, indium, and stannous salts are especially preferred. Mixtures of the amino carboxylate compounds can also be used.

Similar amino carboxylates, including ethylenediaminetetraacetic acid and iminodiacetic acid precipitate the bis-biguanide compound.

The concentration of the amino carboxylate com-

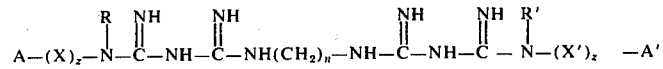

wherein A and A' each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ may optionally be interrupted by oxygen or sulfur atoms, aromatic nuclei, etc. The salts of the above compounds are especially desirable. The water soluble salts are the most desirable since it is then possible to form clear pound in the oral compositions of this invention can range from about 0.10% to about 1.25% by weight in excess of the amount which will react with the bis-biguanide compound present. Within the pH range of the oral compositions of the present invention, it is to be understood that the amino carboxylate compounds react with the bis-biguanide compounds in the ratio of two moles of amino carboxylate compound to one mole of bis-biguanide compound. Oral compositions which in the ordinary course of usage could be accidentally ingested should contain lower concentrations of amino carboxylate compound. Thus, a mouthwash in accordance with this invention preferably contains less than about 1% by weight of amino carboxylate compound. Dentifrice compositions, topical solutions and prophylaxis pastes, the latter to be administered professionally, can contain up to about 1.25% by weight, preferably from about 0.1% to about 1.0% by weight of amino carboxylate compound. If desired, one can use a lesser amount, so long as it is effective to reduce the stain.

The pH of the compositions of this invention is preferably maintained within the range of from about 4.5 to about 9.5. Below about 4.5, damage to dental enamel can occur. Above about 9.5, the alkalinity becomes cosmetically undesirable and may irritate soft tissue in the mouth. When the amino carboxylate compound is NTA or its salts, the pH is desirably in the range of about 4.5 to about 8.0, preferably about 6.5 to about 7.5. When the amino carboxylate compound is hendic acid or its salts, the pH is desirable in the range of about 4.5 to about 7.5, preferably from about 5.0 to about 7.5. The pH of the compositions of the invention can be adjusted if necessary, by commonly used acidifying agents such as acetic acid, gluconic, acid, etc., or alkalizing agents such as sodium hydroxide, potassium hydroxide, etc.

In addition to the essential components of the oral compositions of this invention as described in the foregoing, such compositions can also contain carriers suitable for use in the oral cavity. Such carriers include the usual components of toothpaste, toothpowder, mouthwash, prophylaxis pastes and the like as more fully described hereinafter.

In addition to the amino carboxylate compound of this invention, it is possible to include a phosphorus-containing anti-calculus agent as disclosed in my co-pending application. Ser. No. 463,495, filed April 24, 1974, for ORAL COMPOSITIONS FOR PLAQUE, CARIES, AND CALCULUS RETARDATION WITH REDUCED STAINING TENDENCIES. Said application is incorporated herein by reference. However, if a solution is desired containing water soluble bis-biguanide salt, then the phosphorus-containing anti-calculus agent should not be used since it will form an insoluble salt with the bis-biguanide compound.

A dentifrice, especially toothpaste, containing an anti-calculus agent is a preferred embodiment of this invention. Toothpaste compositions conventionally contain abrasive materials, sudsing agents, binders, humectants, flavoring and sweetening agents.

The abrasive should preferably be one which does not adsorb the bis-biguanide compound.

Suitable sudsing agents are those which are reasonably stable and form suds throughout a wide pH range, and which will not react with the bis-biguanide compound, i.e., non-soap nonionic, cationic, zwitterionic and amphoteric organic synthetic detergents.

The nonionic synthetic detergents which can be used with the oral compositions of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula, $R_1R_2R_3N \rightarrow O$, wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxyl ethyl, or hydroxy propyl radicals. The arrow in the formula is a conventional representation of a semi-polar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetradecylamine oxide, 2-dodecoxyethyldimethylamine oxide, 3-dodecoxy-2-hydroxypropyl-di(3-hydroxypropyl)amine oxide, dimethylhexadecylamine oxide.

5. Long chain tertiary phosphine oxides corresponding to the following general formula $RR'R''P \rightarrow O$ wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond.

Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropyiphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide, 2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide
3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water solubilizing group, e.g., carboxy, sulfonate, sulfate, phosphate, or phosphonate. A general formula for these compounds is:

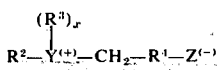

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; $x$ is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-]S-3-hydroxypropyl-S-hexadecylsulfonio]-3-hydroxypentane-1-sulfate;
3-[P,P-diethyl-P-3,6,9-trioxatetradecoxylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]butane-1-carboxylate;
3-[S-ethyl-S-(3-dodecoxy-2-hydroxypropyl)sulfonio]-propane-1-phosphate;
3-[-P,P-dimethyl-P-dodecylphosphonio]-propane-1-phosphonate; and
5-[N,N-di(3-hydroxypropyl)-N-hexadecylammonio]2-hydroxypentane-1-sulfate.

The cationic synthetic detergents useful in the oral compositions of the present invention can be broadly defined as quaternary ammonium compounds having 1 long alkyl chain containing from about 8 to about 18 carbon atoms such as lauryl trimethylammonium chloride; cetyl pyridinium chloride; cetyl trimethylammonium bromide; di-isobutylphenoxyethoxyethyl-dimethylbenzylammonium chloride; coconutalkyltrimethylammonium nitrite; cetyl pyridinium fluoride; etc. Especially preferred are the quaternary ammonium fluorides described in U.S. Pat. 3,535,421 incorporated by reference hereinbefore, where said quaternary ammonium fluorides have detergent properties.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxylate, sulfonate, sulfate, phosphate, or phosphonate. Examples of compounds falling within this definition are sodium 3-dodecylaminopropionate, sodium 3-dodecylaminopropane sulfonate, dodecyl-beta-alanine, N-alkyl-taurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The sudsing agent can be present in the dentifrice compositions of this invention in an amount from 0.5% to 5% by weight of the total compositions.

It is preferable to have a water-soluble fluoride compound present in an amount to give a fluoride concentration of from about 0.0025% to about 5.0%, preferably from about 0.005% to about 2.0%, to provide additional anti-caries effectiveness. Suitable fluoride sources are disclosed in the examples given hereinafter. Preferred fluorides are sodium fluoride, stannous fluoride, indium fluoride, and sodium monofluorophosphate. The fluorides will give an insoluble bis-biguanide salt, however, and should only be used where that is acceptable. U.S. Pat. 3,535,421 and Agricola et al's U.S. Pat. application Ser. No. 329,783, filed Feb. 19, 1973, are incorporated herein by reference.

All parts, percentages and ratios herein are by weight unless otherwise indicated.

In preparing toothpastes, it is ncessary to add some thickening material to provide a desirable consistency. Preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Suitable flavoring agents include oil of wintergreen, oil of peppermint, oil of spearmint, oil of sassafras, and oil of clove. Sweetening agents which can be used include saccharin, dextrose, levulose and sodium cyclamate.

In its method aspect, the present invention comprises a method of reducing dental plaque and/or caries by applying to the oral cavity an effective amount of a composition of the invention. Any amount which is sufficient to achieve the desired reduction is an effective amount. Generally, an amount which supplies at least about 0.001 g. per usage of the bis-biguanide compound is effective.

Several representative oral compositions illustrating this invention are set forth in the following examples.

EXAMPLE I

A solution is prepared containing 0.2 gram chlorhexidine [1,6-di-($N^5$-p-chlorophenyl-$N^1$-diguanido)hexane]digluconate; 1.0 gram disodium nitrilotriacetate (NTA); 0.05 gram acetic acid; and 98.78 grams water, said solution having a pH of about 6.1. No precipitate forms. The resulting clear composition, when used in the mouth, inhibits the formation of plaque, calculus, caries and gingivitis, but with continued use, does not form the large amount of stain that would result if the NTA was not present.

EXAMPLE II 0.025 gram sodium fluoride was added to 100 grams of the solution of Example I. This solution inhibits the formation of plaque and calculus, and in addition, has greater anti-caries effectiveness.

EXAMPLE III

A solution is prepared containing 0.2 gram chlorhexidine digluconate; 1.0 gram sodium hendate; 1.0 gram polyoxyethylene (20) sorbitan monolaurate; 0.036 gram sodium hydroxide; and 97.76 grams water, the solution having a pH of 6.5 This solution, when used in the mouth on a regular basis, inhibits the formation of plaque, calculus and caries without excessive stain formation.

Several mouthwash compositions illustrating this invention are set forth in the following examples.

| Component | Ex. | Percent by Weight | | | | |
|---|---|---|---|---|---|---|
| | | IV | V | VI | VII | VIII |
| Glycerine | | 10.0 | 10.0 | 10.0 | 10.0 | 10.0 |
| Ethyl alcohol | | 16.5 | 16.5 | 16.5 | 16.5 | 16.5 |
| Polyoxyethylene (2) sorbitan monoisostearate | | 1.00 | 1.00 | 1.00 | 1.50 | 2.00 |
| Sodium saccharin | | .045 | .045 | .045 | .045 | .045 |

-continued

| Component | Ex. | Percent by Weight | | | | |
|---|---|---|---|---|---|---|
| | | IV | V | VI | VII | VIII |
| Chlorhexidine digluconate | | 0.1 | 0.15 | 0.15 | 0.15 | 0.15 |
| Flavor | | .088 | .088 | .088 | .088 | .088 |
| Dipotassium NTA | | 0.5 | | | | 0.9 |
| Disodium hendate | | | 0.9 | | | |
| Diammonium hendate | | | | 0.9 | | |
| Stannous nitrilotriacetic acid | | | | | 0.9 | |
| Sodium fluoride | | | | | | 0.10 |
| Water | | balance | | | | |

Adjust pH to 7.

EXAMPLE IX

A tooth powder which constitutes yet another embodiment of this invention has the following formulation:

| Component | Percent by Weight |
|---|---|
| Calcium pyrophosphate | 91.30 |
| Polyoxyethylene (20) sorbitan monolaurate | 1.30 |
| Sodium saccharin | 0.25 |
| Flavoring | 1.45 |
| Chlorhexidine diacetate | 0.70 |
| Disodium nitrilotriacetate | 1.00 |

When diluted with water and brushed upon the teeth in the conventional manner, this composition has a pH of approximately 7.0. The composition retards the formation of plaque, calculus, and caries without excessive staining.

EXAMPLE X

A prophylaxis paste for use in the dental office for removal of stains and polishing the tooth surface after mechanical removal of calculus is formulated as follows:

| Component | Percent by Weight |
|---|---|
| Composition A: | |
| Navajo pumice | 77.1 |
| $TiO_2$ | 4.0 |
| Glycerine | 15.352 |
| Hydroxyethylcellulose | .222 |
| Sodium saccharin | .326 |
| Glycine fluoride | 1.0 |
| Sodium nitrilotriacetate | 2.0 |
| Composition B: | |
| Chlorhexidine digluconate | 2.7 |
| Water | 97.30 |

Immediately prior to use, 5.5 gm. of Composition A are mixed with 5.5 gm. of Composition B to attain the desired texture and adjusted to pH 7.0. The paste is then applied to the tooth surfaces with a rubber prophylactic cup in the conventional manner. This composition inhibits the formation of plaque, calculus, and caries without adverse effects of stain formation.

EXAMPLE XI

A toothpaste prepared in accordance with this invention has the following composition:

| Component | Percent by Weight |
|---|---|
| Precipitated urea/formaldehyde condensate (abrasive) | 31.00 |
| Sorbitol (70% aqueous solution) | 6.25 |

-continued

| Component | Percent by Weight |
|---|---|
| Glycerine | 18.00 |
| Polyoxyethylene sorbitan (20) monoisostearate | 1.50 |
| Hydroxyethylcellulose | 1.15 |
| Magnesium aluminum silicates | 0.40 |
| Sodium saccharin | 0.04 |
| Flavoring | 0.95 |
| Disodium ethane-1-hydroxy-1,1-diphosphonate | 0.50 |
| Sodium nitrilotriacetate | 0.9 |
| Sodium monofluorophosphate | 3.00 |
| Sodium fluoride | 0.03 |
| Chlorhexidine digluconate | 0.15 |
| Water | balance |

Mole ratio polyphosphonate/fluoride about 24.
pH adjusted to 7.5 with 5N.NaOH.

This composition is effective in retarding the formation of dental calculus when used in a conventional manner. This composition also inhibits plaque and caries.

EXAMPLE XII

| Component | Percent by Weight |
|---|---|
| Chlorhexidine digluconate | 0.15 |
| NTA (Na$_2$ salt) | 0.9 |
| Brij. 35 SP | 1.0 |
| Ethanol | 12.0 |
| Glycerol | 6.0 |
| Water | balance |

EXAMPLE XIII

Oral surfaces are treated sequentially with a 02% aqueous solution of chlorhexidine digluconate and a 1% aqueous solution of disodium nitrilotriacetate containing 025% sodium fluoride.

When in the above examples the following water-soluble fluoride agents are substituted, either wholly or in part, for the sodium fluoride, substantially equivalent results are obtained in that the formulas provide additional anti-caries activity: sodium monofluorophosphate, stannous fluoride, potassium fluoride, lithium fluoride, cesium fluoride, ammonium fluoride, indium fluoride, stannous fluorozirconate, lead fluoride, palladium fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolaminoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, $\Delta^{8,9}$-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N'-dilaurylethylene-diammonium difluoride, N-cetylpyridinium fluoride, N:N-dilauryl-morpholinium fluoride, N-myristyl-N-ethylmorpholinium fluoride, N-(octylaminocarbonylethyl)-N-benzyl-dimethylammonium fluoride, N-($\beta$-hydroxydodecyl)trimethylammonium fluoride, N-phenyl-N-hexadecyldimethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzylloxyethyl)N-dodecyldimethylammonium fluoride, N-[2-(N:N'-dimethylaminocarbonyl)-ethyl]-N-dodecyldiethylammonium fluoride, N-carboxymethyl-N-eicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and mixtures thereof in, e.g., 1:1 proportions. The glycine fluorides are preferred.

When in the above examples the following surface-active agents are inserted in an amount of from about 1 to 2% as an additional ingredient, substantially equivalent results are obtained, except that the compositions have enhanced detergency effects: polypropylene glycol (M.W. 1700) polyoxyethylene (M.W. 1500); polyoxypropylene (70) ethylenediamine polyoxyethylene (100); coconut alcohol polyoxyethylene (20); dimethyldodecylamine oxide; oleyldi(2(2-hydroxyethyl)amine oxide; dimethyloctylamine oxide; dimethyldecylamine oxide; dimethyltetradecylamine oxide; 3,6,9-trioxaheptadecyldiethylamine oxide; di(2-hydroxyethyl)tetradecylamine oxide; 2-dodecoxyethyldimethylamine oxide; 3-dodecoxy-2-hydroxypropyldi(3-hydroxypropyl)amine oxide; dimethylhexadecylamine oxide; dodecyldimethylphosphine oxide; tetradecyldimethylphosphine oxide; tetradecylmethylethylphosphine oxide; 3,6,9-trioxaoctadecyldimethylphosphine oxide; cetyldimethylphosphine oxide; 3-dodecoxy-2-hydroxypropyldi(2-hydroxyethyl)phosphine oxide; stearyldimethylphosphine oxide; cetylethylpropylphosphine oxide; oleyldiethylphosphine oxide; dodecyldiethylphosphine oxide; tetradecyldiethylphosphine oxide; dodecyldipropylphosphine oxide; dodecyldi(hydroxymethyl)phosphine oxide; dodecyldi(2-hydroxyethyl)phosphine oxide; tetradecylmethyl-2-hydroxypropylphosphine oxide; oleyldimethylphosphine oxide; 2-hydroxydodecyldimethylphosphine oxide; octadecyl methyl sulfoxide; 2-ketotridecyl methyl sulfoxide; 3,6,9-trioxaoctadecyl 2-hydroxyethyl sulfoxide; dodecyl methyl sulfoxide; oleyl 3-hydroxypropyl sulfoxide; tetradecyl methyl sulfoxide; 3-methoxytridecyl methyl sulfoxide; 3-hydroxytridecyl methyl sulfoxide; 3-hydroxy-4-dodecoxybutyl methyl sulfoxide; 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetradecoxylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl) ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; 5-[N,N-di(3-hydroxypropyl)-N-hexadecylammonio]2-hydroxypentane-1-sulfate; dodecyltrimethylammonium chloride; nonylbenzylethyldimethylammonium nitrate; tetradecylpyridinium bromide; octadecylbutylpropylmethylphosphonium nitrite; decyldimethylsulfonium chloride; (hexylphenyl)dimethylbenzylammonium fluoride; eicosyldimethylbenzylphosphonium chloride; coconut-alkylmethylmorpholinium nitrate; octadecylmethylbenzylsulfonium sulfate; laurylpyridinium chloride; laurylpyridinium bromide; laurylpyridinium bisulfate; laurylpyridinium-5-chloro-2-mercaptobenzothiazole; laurylpicolinium-p-toluenesulfonate; tetradecylpyridinium bromide; cetylpyridinium chloride; cetylpyridinium bromide; laurylisoquinolinium bromide; laurylisoquinolinium saccharinate; alkylisoquinolinium bromide; N-cetyl-N-ethyl-morpholinium ethosulfate; benzalkonium chloride; monoquaternaries $R_4N^+X^-$ (one R group is fatty); octadecyltrimethylammonium chloride; coconut alkyl trimethylammonium chloride; dodecylbenzyltri(octyldecyl)ammonium chloride; monoquaternaries $R_4N^+X^-$ (two R groups are fatty); dihexadecyldimethylammonium chloride; dicoconut alkyl dimethylammonium chloride; monoquaternaries $R_4N^+X^-$ (three R groups are fatty); tri(hydrogenated tallow) methylammonium chloride; distilled tallow amine acetate; diamine acetates; N-oleyl propylene diamine monoacetate; condensation product of octyl phenol with 15 moles of ethylene oxide per mole of octyl phenol; dimethyldodecylamine oxide; dodecyldimethylphosphine oxide; tetradecyl methyl sulfoxide; 3-(N,N-dimethyl-N-hexadecylammonio)propane-1-sulfonate; 3-dodecylaminopropionate; and dodecyl-beta-alanine.

When in the above examples, the following bis-biguanide compounds are substituted, either wholly or in part (50%) for the preferred chlorhexidine digluconate, substantially equivalent results are obtained in that plaque, calculus, caries and gingivitis are inhibited with reduced staining as compared to the use of the bis-biguanide compounds alone 1,6-bis-(2-ethylhexylbiguanidohexane)dihydrochloride; 1,6-di-($N^5$-phenyl-$N^1$-diguanido)hexane tetrahydrochloride; 1,6-di-($N^5$-phenyl-$N^5$-methyl-$N^1$-diguanido)hexane dihydrochloride; 1,6-di($N^5$-o-chlorophenyl-$N^1$-diguanido)hexane dihydrochloride; 1,6-di($N^5$-2,6-dichlorophenyl-$N^1$-diguanido)-hexane dihydrochloride; 1,6-di[$N^5$-p-methoxyphenyl-$N^1$-diguanido]hexane dihydrochloride; 1,6-di-($N^5$-p-nitrophenyl-$N^1$-diguanido)hexane dihydrochloride; $\omega,\omega'$-di($N^5$-phenyl-$N^1$-diguanido)-di-n-propylether dihydrochloride; $\omega,\omega'$-di ($N^5$-p-chlorophenyl-$N^1$-diguanido)-di-n-propylether tetrahydrochloride; 1,6-di($N^5$-2,4-dichlorophenyl-$N^1$-diguanido)hexane tetrahydrochloride; 1,6-di-($N^5$-p-methylphenyl-$N^1$-diguanido) hexane dihydrochloride; 1,6-di-($N^5$-2,4,5-trichlorophenyl-$N^1$-diguanido)hexane tetrahydrochloride; 1,6-di[$N^5$-alpha-(p-chlorophenyl)ethyl-$N^1$-diguanido]hexane dihydrochloride; $\omega,\omega'$-di($N^5$-p-chlorophenyl-$N^1$-diguanido)m-xylene dihydrochloride; 1,12-di-($N^5$-p-chlorophenyl-$N^1$-diguanido) dodecane dihydrochloride; 1,10-di($N^5$-phenyl-$N^1$-diguanido) decane tetrahydrochloride; 1,12-di($N^5$-phenyl-$N^1$-diguanido) dodecane tetrahydrochloride; 1,6-di($N^5$-p-chlorophenyl-$N^1$-diguanido)hexane tetrahydrochloride; ethylene bis (1-tolyl biguanide); ethylene bis (p-tolyl biguanide); ethylene bis(3,5-dimethylphenyl biguanide); ethylene bis(p-tolyl biguanide;ethylene bis(3,5-dimethylphenyl biguanide); ethylene bis(p-tert-amylphenyl biguanide); ethylene bis(nonylphenyl biguanide); ethylene bis (phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenyl biguanide); ethylene bis(mixed amyl naphthyl biguanide); N-butyl ethylene bis(phenyl biguanide); trimethylene bis(o-tolyl biguanide); N-butyl trimethylene bis(phenyl biguanide); tetramethylene bis(1-tolyl biguanide); the specific compounds disclosed in U.S. Pat. No. 2,863,919, Birtwell et al., (Dec. 9, 1958), said patent being incorporated herein by reference; the specific compounds disclosed in U.S. Pat. No. 3,468,898, Cutler et al., (Sept. 23, 1969), said patent being incorporated herein by reference; and the corresponding pharmaceutically acceptable salts of all of the above such as the acetates; gluconates; hydrochlorides; hydrobromides; citrates; bisulfites; fluorides; polymaleates; N-coconut alkyl sarcosinates; phosphites; hypophophites, perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; perfluoropropionates; and the salts prepared by reacting the following salts with the bis-biguanide compounds: disodium ethane-1-hydroxy-1,1-diphosphonate; disodium salt of ethane-1,2-dicarboxy-1,2-diphosphonic acid; dipotassium salt of ethane-1,2-dicarboxy-1,2-dihydroxy-1,2-diphosphonic acid; the monocalcium salt of ethene-1,2-dicarboxy-1-phosphonic acid; the monomagnesium salt of ethane-1,2-dicarboxy-1-hydroxy-1,1-diphosphonic acid; the di(triethanolammonium) salt of ethane-1,2-dicarboxy-1,2-diphosphonic acid; the disodium salt of ethane-1,2-dicarboxy-1,2-diphosphonic acid; diammonium salt of ethane-1,2-dicarboxy-1,2-diphosphonic acid; monocalcium salt of ethane-1,2-dicarboxy-1,2-dihydroxy-1,2-diphosphonic acid; distannous salt of ethane-1,2-dicarboxy-1-hydroxy-1,2-diphosphonic acid; indium salt of ethene-1,2-dicarboxy-1-phosphonic acid; triammonium salt of ethane-1,2-dicarboxy-1,2-dihydroxy-1,2-diphosphonic acid; trisodium salt of ethene-1,2-dicarboxy-1-phosphonic acid; distannous salt of ethane-1,2-dicarboxy-1,2-diphosphonic acid; hexasodium salt of cyclic tetraphoxphonic acid; trisodium salt of methanecyclohexylhydroxydiphosphonic acid; diammonium salt of methanecyclobutylhydroxydiphosphonic acid; monocalcium salt of methanecyclopentylhydroxydiphosphonic acid; distannous salt of methanecycloheptylhydroxydiphosphonic acid; indium salt of methanecyclooctylhydroxydiphosphonic acid; triaamonium salt of methanecyclononylhydroxydiphosphonic acid; trisodium salt of methanecyclodecylhydroxydiphosphonic acid; distannous salt of methanecyclohexylhydroxydiphosphonic acid; methanecycloalkylhydroxydiphosphonic acid; tris(1-phosphonoethyl)amine; tetrasodium salt of tris(2-phosphono-2-propyl)amine; dipotassium salt of bis(phosphonomethyl)-1-phosphonoethyl amine; monocalcium salt of bis(phosphonomethyl)-2-phosphono-2-propyl amine; monomagnesium salt of bis(1-phosphonoethyl)phosphonomethyl amine; distannous salt of bis(2-propyl)phosphonomethyl amine; Victamide and mixtures thereof, e.g., 1:1 and 1:1:1 ratios.

What is claimed is:

1. An oral composition effective in inhibiting bis-biguanide tooth staining and the formation of plaque, caries and calculus comprising a carrier suitable for use in the oral cavity, and A. from about 0.01% to about 2.5% by weight of a tooth-staining bis-biguanide compound, otherwise tending to produce a rather offensive brown tooth stain, and having the generic formula:

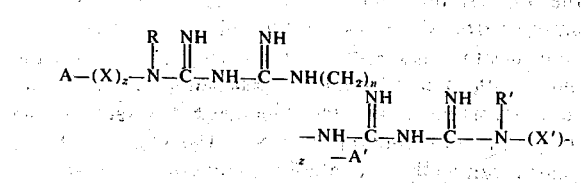

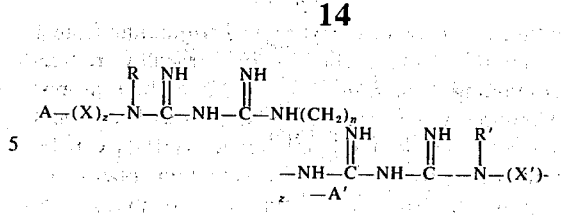

wherein A and A' each represent either (1) a phenyl radical which can contain as substituents up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl, or naphthyl moieties; or the pharmaceutically acceptable salts thereof; and b. from about 0.10% to about 1.25% by weight, in excess of the molar amount which will react with the bis-biguanide compounds of an amino carboxylate compound which in said concentration range effectively reduces said bis-biguanide tooth stain, without precipitating said tooth-staining bis-biguanide, and which is selected from the group consisting of nitrilo triacetic acid and its pharmaceutically acceptable water-soluble salts; said composition having a pH of from about 4.5 to about 8.0.

2. The composition of claim 1 wherein the bis-biguanide compound is a water-soluble salt.

3. The composition of claim 2 wherein the pH is from about 6.5 to about 7.5.

4. The composition of claim 2 containing a water-soluble source of fluoride in a quantity sufficient to provide fluoride in an amount of from about 0.0025% to about 5.0% as $F^-$.

5. The composition of claim 2 containing from about 0.05% to about 1.2% by weight of the bis-biguanide compound and from about 0.1% to about 1% by weight of the amino carboxylate compound.

6. The composition of claim 2 wherein the bis-biguanide compound is [1,6-di-($N^5$-p-chlorophenyl-$N^1$-diguanido) hexane] digluconate, and the aminocarboxylate compound is disodium nitrilotriacetate.

7. The composition of claim 2 wherein the bis-biguanide compound is present as a pharmaceutically acceptable salt selected from the group consisting of the hydrochloride, acetate, and gluconate salts.

8. The composition of claim 2 wherein A - $(X)_z$ is an ethylhexyl group and $n$ is 6.

9. The composition of claim 2 wherein A and A' are each p-chlorophenyl groups, $z$ and $z'$ are 0, and $n$ is 6.

10. The process of inhibiting bis-biguanide tooth staining and dental plaque and caries, comprising the steps of:

A. contacting the oral cavity with a composition comprising a carrier suitable for use in the oral cavity, and a tooth-staining bis-biguanide compound otherwise tending to produce a rather offensive brown tooth stain, upon continuous oral use, and having the generic formula:

wherein A and A' each represent either (1) a phenyl radical which can contain as substituents up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 to 1; wherein R and R' each represent either hydrogen, an alkyl radical containing from 1 to about 12 carbon atoms an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl, or naphthyl moieties; or the pharmaceutically acceptable salts thereof, the amount of said composition being sufficient to provide at least 0.001 grams of the said bis-biguanide compound; and B. contacting said oral cavity with a second composition comprising a carrier suitable for use in the oral cavity, and from about 0.10% to about 1.25% by weight, in excess of the molar amount which will react with the amount of bis-biguanide compound of Step A, of an amino carboxylate compound which in said concentration range effectively reduces said bis-biguanide tooth stain without precipitating said tooth-staining bis-biguanide and which is selected from the group consisting of nitrilo triacetic acid and its pharmaceutically acceptable water-soluble salts; said composition having a pH of from about 4.5 to about 8.0.

11. A process of inhibiting dental plaque and caries comprising the step of contacting the oral cavity with a composition comprising a carrier suitable for use in the oral cavity, and A. from about 0.01% to about 2.5% by weight of a tooth-staining bis-biguanide compound otherwise tending to produce a rather offensive brown tooth stain, upon continuous use, and having the generic formula:

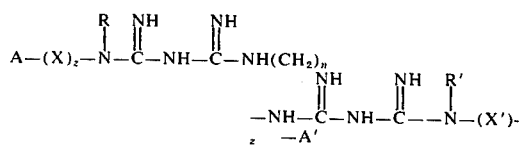

wherein A and A' each represent either (1) a phenyl radical which can contain as substituents up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 to 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl, or naphthyl moieties; or the pharmaceutically acceptable salts thereof; and B. from about 0.01% to about 1.25% by weight, in excess of the molar amount which will react with the tooth-staining bis-biguanide compounds of an amino carboxylate compound which in said concentration range effectively reduces said bis-biguanide tooth stain without precipitating said tooth-staining bis-biguanide and which is selected from the group consisting of nitrilo triacetic acid and its pharmaceutically acceptable water-soluble salts; said composition having a pH of from about 4.5 to about 8.0.

* * * * *